(12) United States Patent
Takino

(10) Patent No.: US 7,147,630 B2
(45) Date of Patent: Dec. 12, 2006

(54) PULL-ON DISPOSABLE WEARING ARTICLE

(75) Inventor: Shunsuke Takino, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 37 days.

(21) Appl. No.: 10/995,896

(22) Filed: Nov. 24, 2004

(65) Prior Publication Data

US 2005/0070869 A1 Mar. 31, 2005

Related U.S. Application Data

(63) Continuation of application No. PCT/JP2003/009188, filed on Jul. 18, 2003.

(30) Foreign Application Priority Data

Aug. 7, 2002 (JP) .............................. 2002-229351

(51) Int. Cl.
*A61F 13/15* (2006.01)
(52) U.S. Cl. ............................ 604/385.201; 604/385.01
(58) Field of Classification Search ........... 604/385.01, 604/385.201, 385.19, 385.02, 385.23, 385.24, 604/385.25, 385.26; 206/494, 497
See application file for complete search history.

(56) References Cited

U.S. PATENT DOCUMENTS

| | | | | |
|---|---|---|---|---|
| 3,744,494 A | * | 7/1973 | Marsan | 604/378 |
| 3,924,627 A | * | 12/1975 | Nystrand | 604/365 |
| 3,943,930 A | * | 3/1976 | Schaar | 604/365 |
| 3,968,799 A | * | 7/1976 | Schrading | 604/365 |
| 4,100,922 A | * | 7/1978 | Hernandez | 604/365 |

FOREIGN PATENT DOCUMENTS

| | | | |
|---|---|---|---|
| EP | 0988846 | * | 3/2000 |
| JP | 3021190 U | | 11/1995 |
| JP | 10-095481 | | 4/1998 |
| JP | 11-104177 | | 4/1999 |
| JP | 11-155904 | | 6/1999 |

* cited by examiner

*Primary Examiner*—Jacqueline F. Stephens
(74) *Attorney, Agent, or Firm*—Lowe Hauptman & Berner LLP

(57) ABSTRACT

An article is formed with a pair of first longitudinal fold guiding lines and a pair of second longitudinal fold guiding lines. A first zone defined between the first fold guiding lines is tucked inwardly of the article along the first fold guiding lines and a second zone defined between the second fold guiding lines is tucked inwardly of the article along the second fold guiding lines. Leg-holes remain opened.

6 Claims, 8 Drawing Sheets

PULL-ON DISPOSABLE WEARING ARTICLE

BACKGROUND OF THE INVENTION

The present invention relates to a pull-on disposable wearing article adapted to absorb and to retain bodily discharges.

There has already been proposed a pull-on disposable wearing article defining front and rear waist regions opposed to each other and a crotch region extending between these waist regions, on one hand, and comprising a liquid-pervious topsheet, a liquid-impervious backsheet and a liquid-absorbent core interposed between these sheets so as to form a waist-hole and a pair of leg-holes lying below the waist-hole, on the other hand, for example, by Japanese Patent Application Publication Nos. 1999-104177A and 1999-155904A.

The pull-on disposable articles disclosed in the above-cited Publication is folded in two in the crotch region so that the respective inner surfaces of the front and rear waist regions may come in contact with each other. A set of about 16 to 48 individual articles is orderly and compactly packed in a package and sold per such package. For example, when 16 diapers are packed in the package, eight articles are placed one against another to form a row extending in a back-and-forth direction and a pair of such rows are stacked in a vertical direction or arranged side by side. In each of these rows, each pair of the articles adjacent in the back-and-forth direction, substantially entire outer surface defined by the front and rear waist regions and the crotch region of the one article is in contact with the corresponding entire outer surface of the other article. When it is desired to pick up one of these articles, the top wall of the package may be broken and the target one article may be finger-gripped and pulled out from the package toward above the package.

Within the package, the article disclosed by the above-cited Publication is folded in two so that the respective inner surfaces of the front and rear waist regions may come in contact with each other and, in consequence, lateral zones of the crotch region destined to define the respective leg-holes are also folded in two and overlaid so as to close the respective leg-holes. To put the article folded in such state on the wearer's body, it is necessary to broaden the respective leg-holes as the wearer's legs are guided through these leg-holes and therefore a troublesome handling is required to put the article on the wearer's body.

In addition, within the package packing a plurality of the articles as disclosed by the above-cited Publication, these articles are compressed together in the back-and-forth direction under a pressure in a range of approximately 15 to 70 N exerted thereon in the back-and-forth direction from longitudinally opposite ends of the row. As a result, a predetermined force is required to pull one of the articles out from the row. These articles are held in contact one with another substantially over the entire outer surface defined by the front and rear waist regions and the crotch region of each of the articles. In other words, the contact area between each pair of the articles adjacent in the back-and-forth direction is relatively large and a frictional force between these articles is correspondingly high. Inconveniently, a force in a range of 20 to 22 N is required to pull the first article out from the row.

SUMMARY OF THE INVENTION

It is an object of the present invention to provide a pull-on disposable wearing article improved so that wearer's legs can be easily guided through respective leg-holes, on one hand, and each of the articles in any one row packed in a package can be easily pulled out from the row.

According to the present invention, there is provided a pull-on disposable wearing article having front and rear waist regions opposed to each other and a crotch region extending between the waist regions connected to each other along transversely opposite lateral zones thereof so as to form a waist-hole and a pair of leg-holes.

The improvement according to the present invention is characterized in that the article is formed with a pair of first longitudinal fold guiding lines extending from a transversely middle zone of the crotch region so as to be spaced apart from each other and further extending in a longitudinal direction over a transversely middle zone of the front waist region and a pair of second longitudinal fold guiding lines extending from the transversely middle zone of the crotch region so as to be spaced apart from each other and further extending in the longitudinal direction over a transversely middle zone of the rear waist region; and a first zone defined between the first fold guiding lines is tucked inwardly of the article along the first fold guiding lines and a second zone defined between the second fold guiding lines is tucked inwardly of the article.

According to one preferred embodiment of the present invention, the article comprises a liquid-pervious topsheet facing a wearer's body, a liquid-impervious backsheet-facing away from the wearer's body and a liquid-absorbent core interposed between these sheets and extending over said crotch region into the front and rear waist regions.

According to another preferred embodiment of the present invention, the core is formed with a longitudinal fold guiding zone extending in the first and second zones and the core has a stiffness lower in the fold guiding zone than in the remaining zone of the core except for the fold guiding zone.

According to still another preferred embodiment of the present invention, a plurality of the articles are compactly packed in a package within which the articles are placed one against another in one direction to form a row so that each pair of the articles adjacent to each other in the one direction are held in contact with each other over respective zones except for said first and second zones, within the package, a force in a range of 10 to 75 N is exerted inward in one direction between opposite ends of the row and a force of 18 N or lower is enough to pull one of the articles out from the row. "A plurality of the articles" is used to refer to approximately eight or more articles.

DETAILED DESCRIPTION OF THE PREFERRED EMBODIMENTS

Details of the pull-on disposable wearing article according to the present invention will be more fully understood from the description given hereunder with reference to the accompanying drawings.

Figure 1:
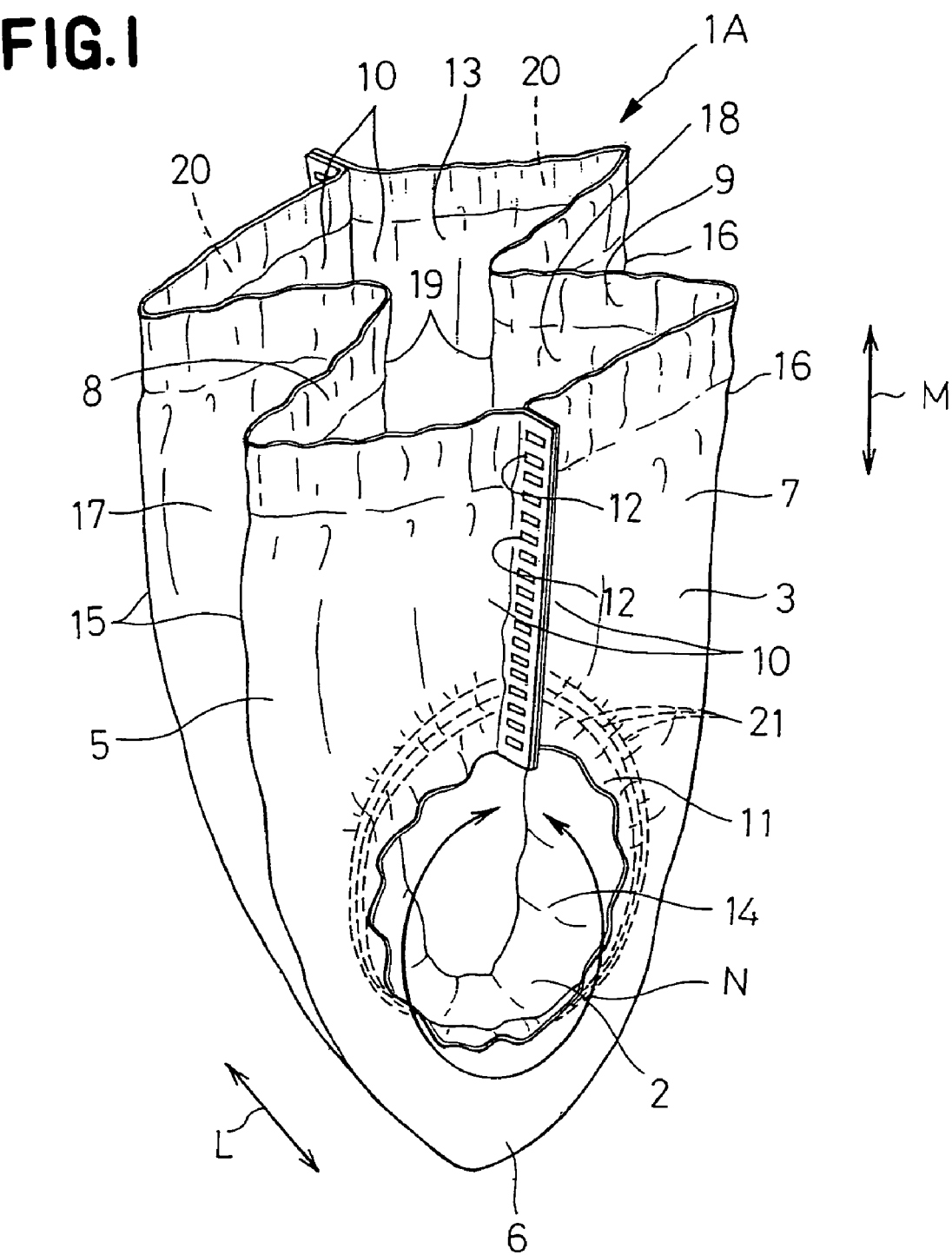
FIG. 1 is a perspective view showing an example of a wearing article.
Figure 2:
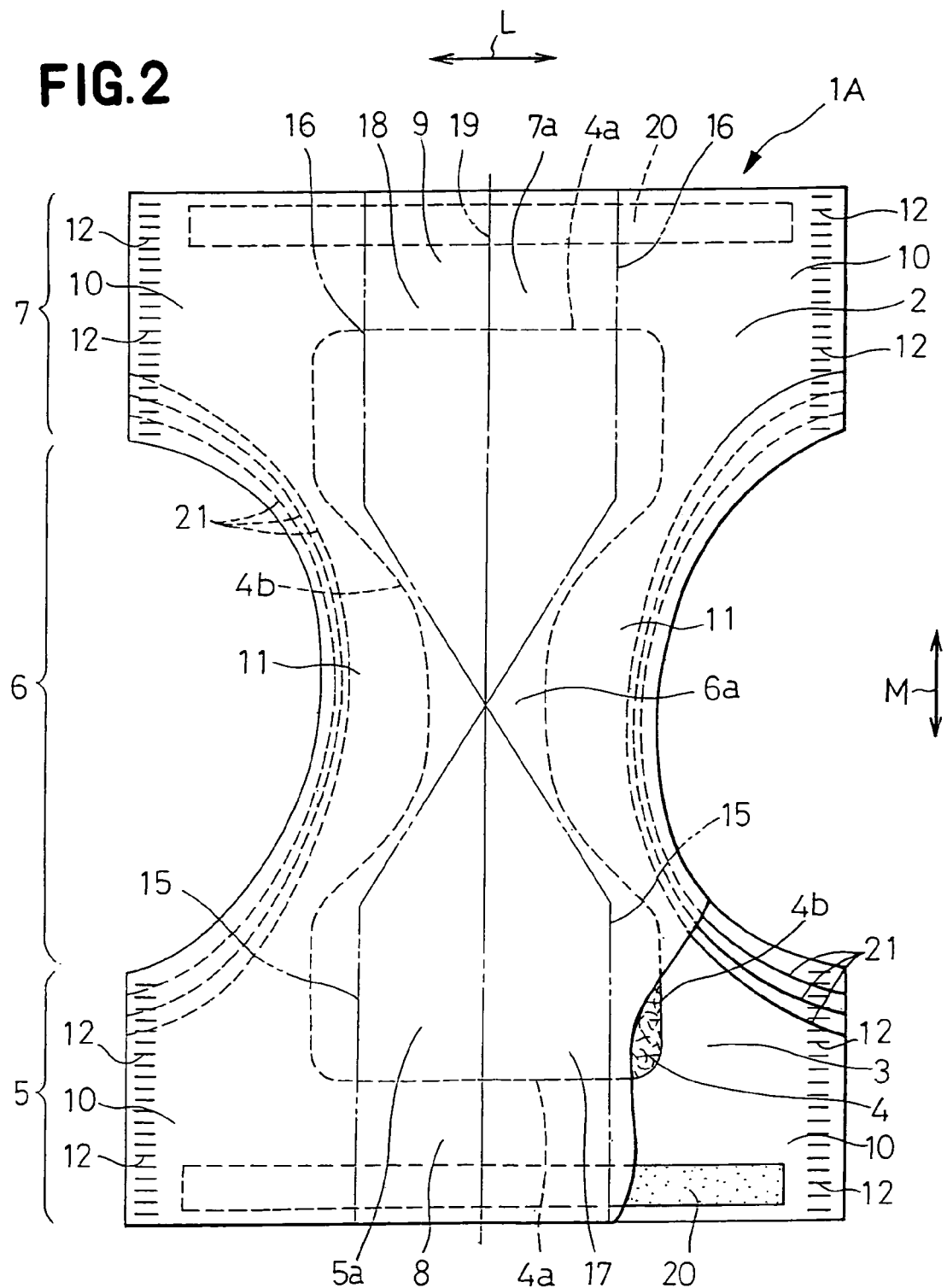
FIG. 2 is a partially cutaway developed plan view showing the article.

FIG. 1 is a perspective view showing a wearing article 1A according to the present invention and FIG. 2 is a partially cutaway developed plan view showing the article 1A, in which its front and rear waist regions are disconnected from each other along transversely opposite lateral zones 10 of these waist regions. In FIGS. 1 and 2, a transverse direction is indicated by an arrow L, a longitudinal direction is indicated by an arrow M and a leg-surrounding direction is indicated by an arrow N (only in FIG. 1). Expression "inner surfaces of top- and backsheets 2, 3" refers to the surfaces of the respective sheets 2, 3 facing a core 4 and expression "outer surfaces of these sheets 2, 3" refers to the surfaces of the respective sheets 2, 3 facing away from the core 4.

The article 1A comprises the liquid-pervious topsheet 2, the liquid-impervious backsheet 3 and the liquid-absorbent core 4 interposed between these sheets 2, 3 and attached to the inner surface of at least one of these sheets 2, 3.

The article 1A has a front region 5, a rear waist region 7 and a crotch region 6 extending between these waist regions 5, 7. The core 4 extends from the crotch region 6 toward the front and rear waist regions 5, 7. The article 1A is contoured by upper end zones 8, 9 of the front and rear waist regions 5, 7 extending outside longitudinally opposite ends 4a, 4a of the core 4 in the transverse direction, transversely opposite lateral zones 10 of the front and rear waist regions 5, 7 extending outside transversely opposite side edges 4b, 4b of the core 4 in the longitudinal direction, and lateral zones 11 of the crotch region 6 extending outside the transversely opposite side edges 4b of the core 4 in the leg-surrounding direction.

In the article 1A, the respective waist lateral zones 10 of the front and rear waist regions 5, 7 are overlaid and joined together by a plurality of heat-sealing lines 12 arranged intermittently along the respective lateral zones 10 in the longitudinal direction. The article 1A is formed with a waist-hole 13 and a pair of leg-holes 14 lying below the waist-hole 13. The respective leg-surrounding lateral zones 11 of the crotch region 6 describe circular arcs which are convex inward in the transverse direction of the article 1A. The article 1A presents a substantially hourglass-like planar shape.

As will be seen in FIG. 2, the article 1A is formed with a pair of first longitudinal fold guiding lines 15 and a pair of second longitudinal fold guiding lines 16. The first fold guiding lines 15 extend from a transversely middle zone 6a of the crotch region 6 so as to be spaced apart from each other and further extend in the longitudinal direction parallel to each other in a transversely middle zone 5a of the front waist region 5. The first fold guiding lines 15 extend from the crotch region 6 to the waist-surrounding end zone 8 of the front waist region 5 over the transversely middle zone 5a of the front waist region 5. The second fold guiding lines 16 extend from the transversely middle zone 6a of the crotch region 6 so as to be spaced apart from each other and extend longitudinally parallel to each other in a transversely middle zone 7a of the rear waist region 7. The second fold guiding lines 16 extend from the crotch region 6 to the waist-surrounding end zone 9 of the rear waist region 7 over the transversely middle zone 7 of the rear waist region 7. The first and second fold guiding lines 15, 16 are converged at the transversely middle zone 6a of the crotch region 6.

A first zone 17 is defined between the first fold guiding lines 15 and extends in the longitudinal direction. Similarly, a second zone 18 is defined between the second fold guiding lines 16 and extends in the longitudinal direction. The first zone 17 is tucked inwardly of the article 1A along the first fold guiding lines 15 so that the outer surface of the backsheet 3 in this first zone 17 is opposed to itself and the first zone 17 gets near to the rear waist region 7. The second zone 18 is tucked inwardly of the article 1A along the second fold guiding lines 16 so that the outer surface of the backsheet 3 in this second zones 18 is opposed to itself and the second zone 18 gets near to the front waist region 5. In the first and second zones 17, 18, an imaginary fold guiding line 19 bisecting respective widths of the first and second zones 17, 18 lies.

Band-like waist elastic members 20 are attached to the respective waist-surrounding end zones 8, 9 so that these elastic members 20 extend in the transverse direction and can contract in this direction. A plurality of leg elastic members 21 are attached to each of the leg-surrounding lateral zones 11 so that these elastic members 21 extend in the leg-surrounding direction and can contract in this direction. These elastic members 20, 21 are interposed between the top- and backsheets 2, 3 and bonded to the inner surface of at least one of these sheets 2, 3. Along the waist-surrounding end zones 8, 9, the waist lateral zones 10 and the leg-surrounding lateral zones 11, the top- and backsheets 2, 3 are overlaid and have the respective inner surfaces intermittently joined together.

Tucking of the first and second zones 17, 18 inwardly of the article 1A along the first and second fold guiding lines 15, 16 allows the article 1A to be made substantially compact. In the article 1A in which the first and second zones 17, 18 are tucked inwardly of the article 1A, the leg-surrounding lateral zones 11 are not overlaid and the leg-holes 14 remain opened. With the article 1A in which the leg-holes 14 are opened, it is unnecessary to open out these leg-holes 14 when the wearer's legs are guided through these leg-holes 14 and it is not likely that any troublesome handling might be required to put the article 1A on the wearer's body.

Figure 3:
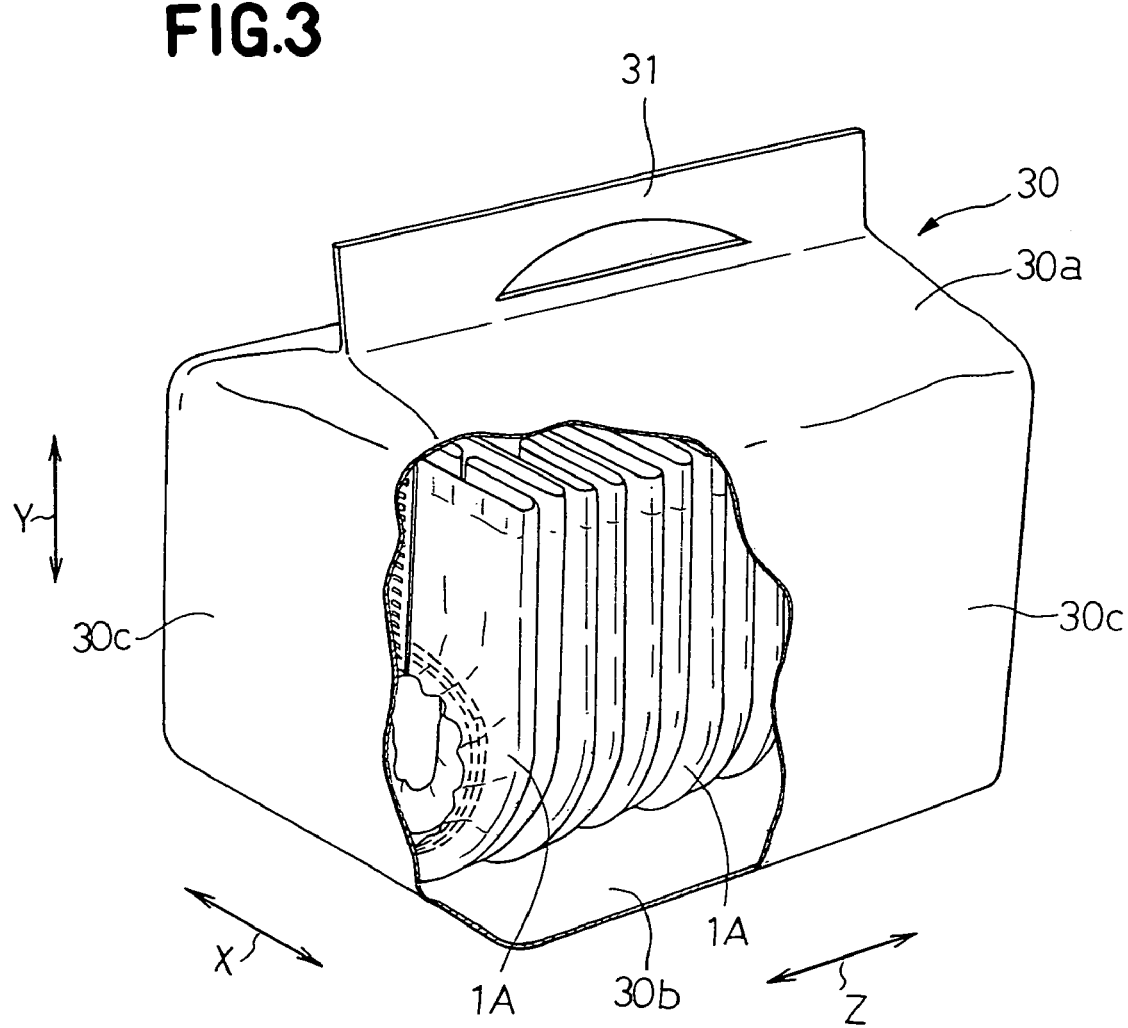
FIG. 3 is a partially cutaway perspective view showing a package packing therein a plurality of the articles each shown in FIG. 1.
Figure 4:
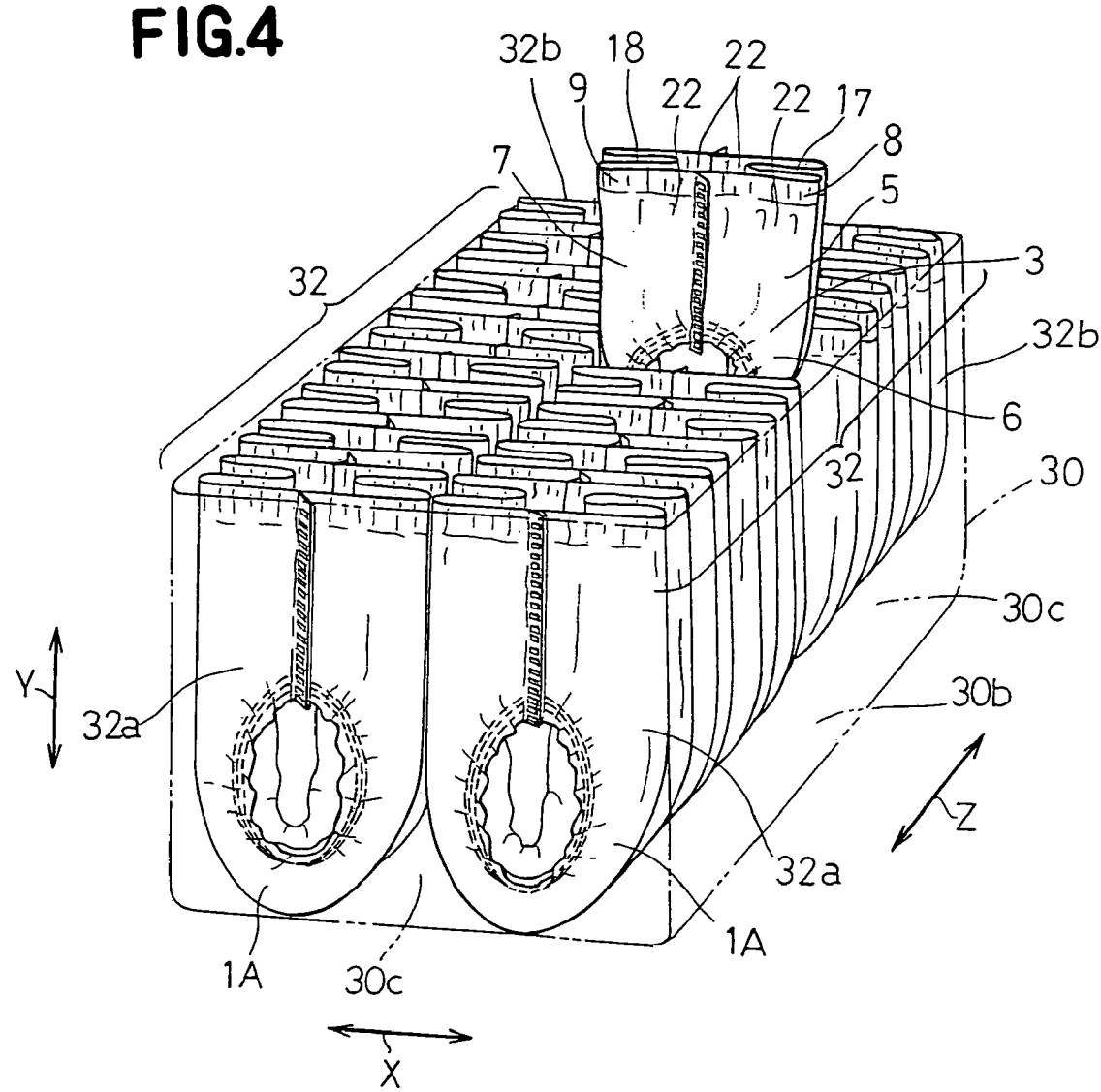
FIG. 4 is a diagram illustrating a manner in which one of the articles is picked up from the package.

FIG. 3 is a partially cutaway perspective view showing a package 30 packing therein a plurality of the articles 1A each shown in FIG. 1 and FIG. 4 is a diagram illustrating a manner in which one of the articles 1A is picked up from the package 30. In FIGS. 3 and 4, a transverse direction is indicated by an arrow X, a longitudinal direction is indicated by an arrow Y and a back-and-forth direction is indicated by an arrow Z. In FIG. 4, the package 30 is indicated by imaginary lines.

The package 30 is made of plastic film and comprises top and bottom walls 30a, 30b and four side walls 30c so as to define a rectangular parallelepiped which is relatively long in the back-and-forth direction. The top wall 30a of the package 30 is formed with a handgrip 31. Within the package 30, the sixteen articles 1A are compactly packed.

Within the package 30, eight articles 1A are placed one against another in the back-and-forth direction so as to form a row 32 and a pair of the rows 32 are packed side by side. In each of the rows 32, each pair of the articles 1A adjacent to each other in the back-and-forth direction are held in contact with each other over remaining zones 22 except for the first and second zones 17, 18 in the respective articles 1A. In the remaining zones 22, these articles 1A are held in contact one with another on the outer surfaces of the backsheets 3.

Within the package 30, these articles 1A are packed under compression in the back-and-forth direction and a force in a range of 10 to 75 N is exerted between opposite ends 32*a*, 32*b* of the row 32 inward in the back-and-forth direction (i.e., inward in one direction). The force exerted between the opposite ends 32*a*, 32*b* of the row 32 inward in the back-and-forth direction is preferably in a range of 20 to 45 N. To pick up one of these articles 1A from the package 30, the top wall 30*a* of the package 30 may be broken as illustrated in FIG. 4, then one of the articles 1A in the row 32 may be finger-gripped and pulled out upward from the package 30. Alternatively, the side wall 30*c* of the package 30 may be broken, then one of the articles 1A in the row 32 may be finger-gripped and pulled out laterally from the package 30.

If the force is lower than 10 N, the row 32 is apt to lean forward or rearward within the package 30 and, when a plurality of the packages 30 are stacked in the vertical direction, such stack of the packages 30 may unintentionally collapse. If the force exceeds 75 N, it is impossible to pull the article 1A smoothly out from the associated row 32.

The force exerted inward in the back-and-forth direction (inward in one direction) between opposite ends 32*a*, 32*b* of the row 32 was measured in a manner as follows: (1) Eight articles 1A with the first and second zones 17, 18 tucked inward were arranged in the back-and-forth direction (in one direction) to form the row 32 and left for 24 hours in a state of nature without exerting a force between the opposite ends 32*a*, 32*b* of the row 32 inward in the back-and-forth direction (inward in one direction). In this row 32, the articles 1A were in contact one with another in the remaining zones 22 except for the first and second zones 17, 18. The row 32 in which a force is not exerted inward in the back-and-forth direction (inward in one direction) had a dimension measured in the back-and-forth direction larger than a dimension of the package 30 in the back-and-forth direction; (2) After left for 24 hours, a pair of plates were placed at the opposite ends 32*a*, 32*b* of the row 32, respectively, so as to sandwich the row 32. Then a plurality of the articles 1A were compressed by the plates inward in the back-and-forth direction (inward in one direction) until the dimension of the row 32 measured in the back-and-forth direction exactly coincided with the dimension of the package 30 measured in the back-and-forth direction; (3) A force exerted upon the plates when the dimension of the row 32 measured in the back-and-forth direction exactly coincides with the dimension of the package 30 measured in the back-and-forth direction was measured by a compression tester; and (4) as the compression tester, INSTRON 5564 (supplied from INSTRON CORP.) was used. A test speed of this compression tester was 10 mm/min. As the plates, acryl plates each having a surface area larger than the exposed area of the article 1A so that the plates may compress the entire exposed area of the remaining zone 22 of the article 1A. It should be understood here that the dimension of the row 32 measured in the back-and-forth dimension when it exactly coincides with the dimension of the package 30 measured in the back-and forth direction refers to the dimension defined between the pair of acryl plates.

In the case of this package 30, a force of 18 N or lower is enough to pull one of the articles 1A out from the row 32 and a force in a range of 15 to 18 N is enough to pull the first article 1A out from the row 32. If a force higher than 18 N is necessary to pull one of the articles 1A out from the row 32, the article 1A could not be smoothly pulled out from the package 30 unless the article 1A is pull with a considerably high force. In addition to such inconvenience, there is a possibility that one or two articles 1A adjacent to the target article 1A might be pulled out from the row 32 as the target article 1A is pulled out from the row 32.

A force necessary to pull the article 1A out from the row 32 was measured in a manner as follows: (1) Eight article 1A with the first and second zones 17, 18 tucked inward were packed within the package 30 so as to be placed one against another in the back-and-forth direction (in one direction). Within the package 30, the remaining zones 22 of the eight articles 1A except for the first and second zones 17, 18 were in contact one with another in the back-and-forth direction to form the row 32, in the same manner as the case illustrated in FIGS. 3 and 4. Within the package 30, a force in a range of 10 to 75 N was exerted inward in the back-and-forth direction from the opposite ends 32*a*, 32*b* of the row 32; (2) A single article 1A was selected from the row 32 and the waist-surrounding end zones 8, 9 were gripped by a chuck of a tensile tester; (3) The article 1A gripped by the chuck was pulled out from the row 32 toward above the package 30 by means of the tensile tester and a force required to pull the article 1A out from the row 32 was measured by the tensile tester; and (4) As the tensile tester, INSTRON 5564 (supplied from INSTRON CORP.) was used. A test speed of the tensile tester was 10 mm/min. It should be understood that the maximum value obtained under the measurement condition as set forth above was defined as the force necessary to draw the article 1A out from the row 32.

The package 30 contains therein a plurality of the articles 1A each having the first and second zones 17, 18 tucked so that an area over which each pair of the adjacent articles 1A held in contact with each other may be reduced and correspondingly a frictional force generated between these adjacent articles 1A may be alleviated compared to the case in which a plurality of articles 1A are packed in the package 30 without being tucked. It is possible to pull the article 1A with a force of 18 N or lower, particularly, to pull the first article 1A out from the row 32 easily regardless of the fact that a force in a range of 10 to 75 N is exerted inward in the back-and-forth direction between the opposite ends 32*a*, 32*b* of the row 32.

Figure 5:
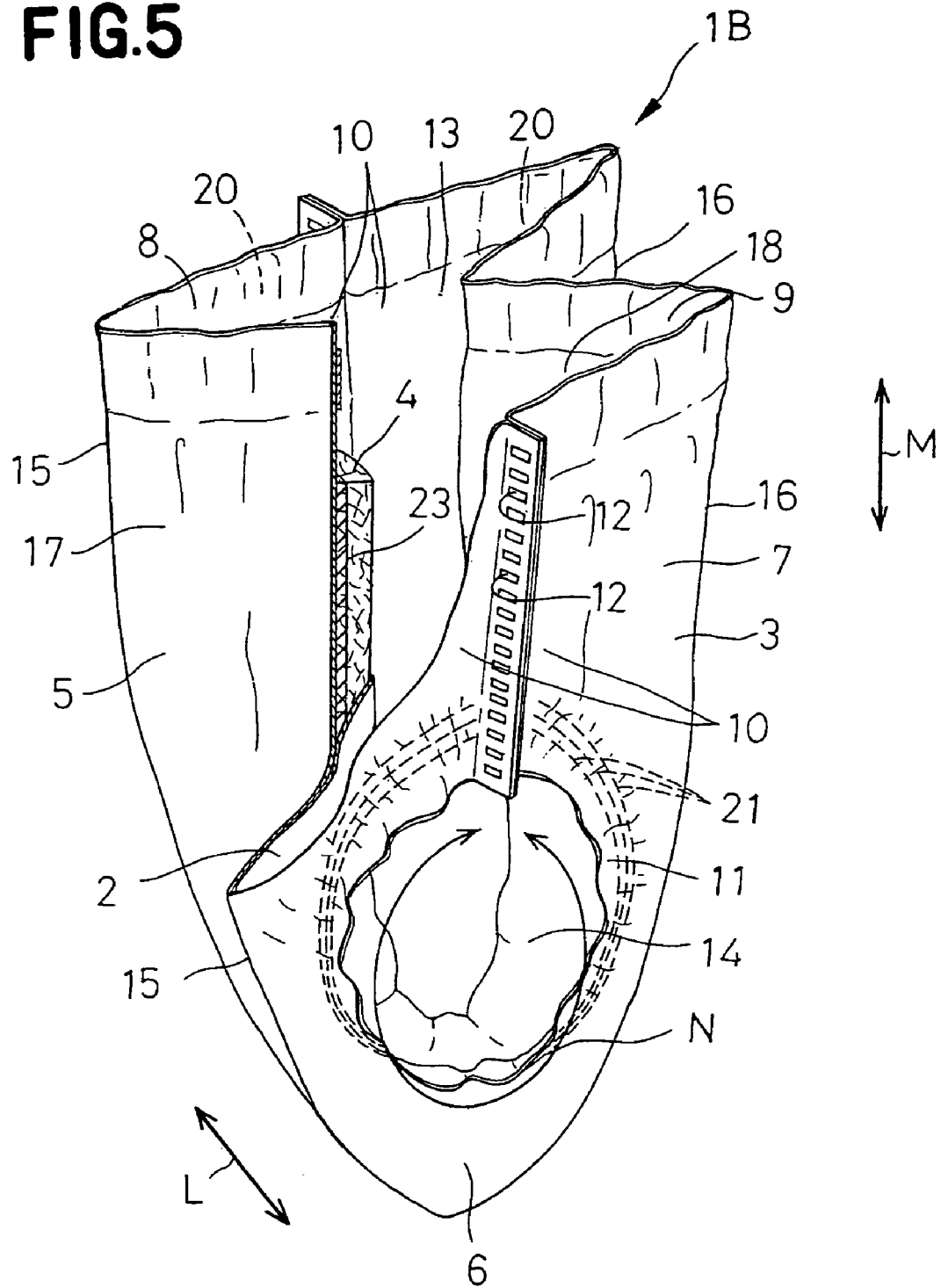
FIG. 5 is a partially cutaway perspective view showing the wearing article according to an alternative embodiment of the invention with its front waist region.
Figure 6:
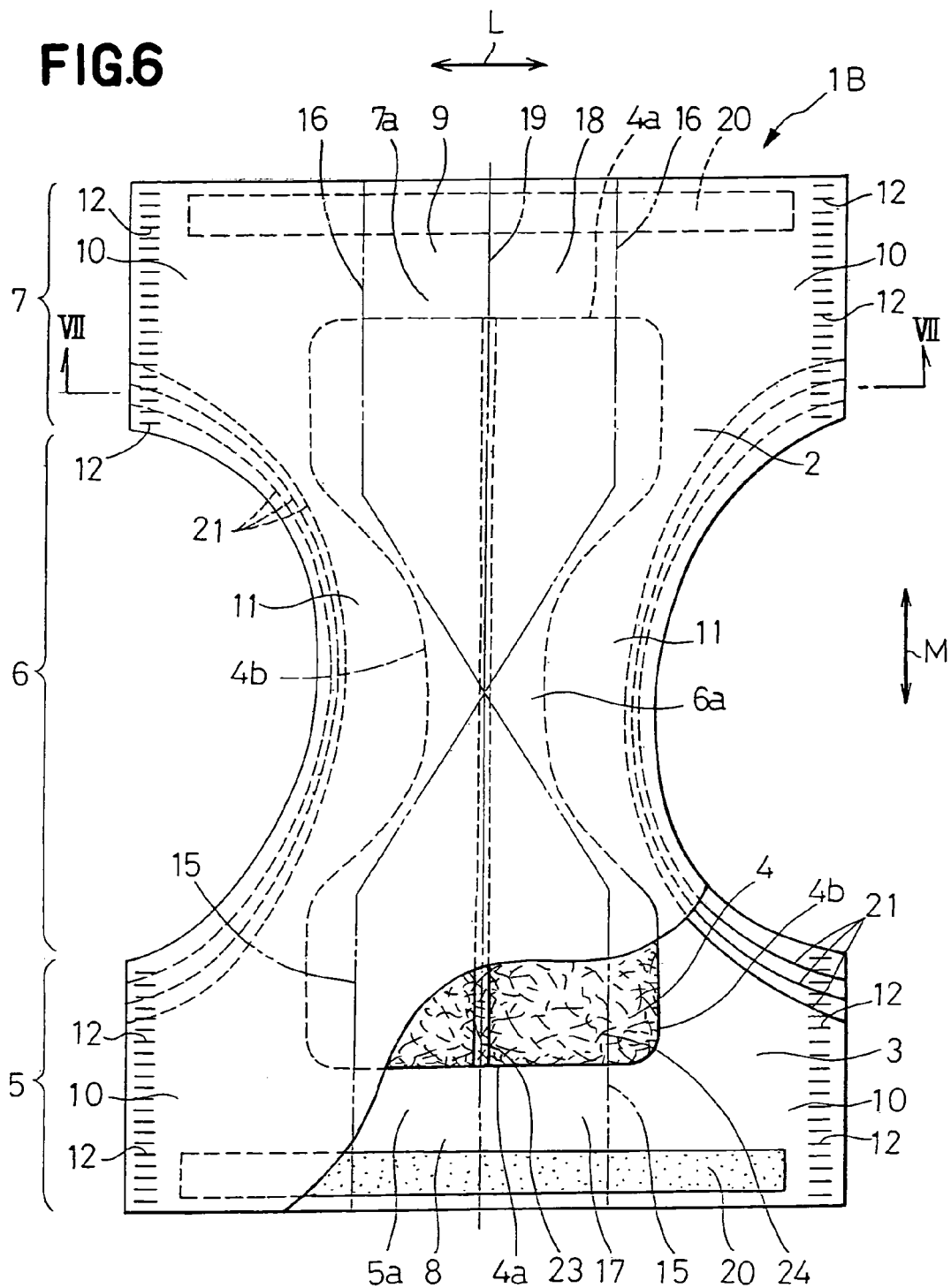
FIG. 6 is a partially cutaway developed plan view showing the article shown in FIG. 5.
Figure 7:
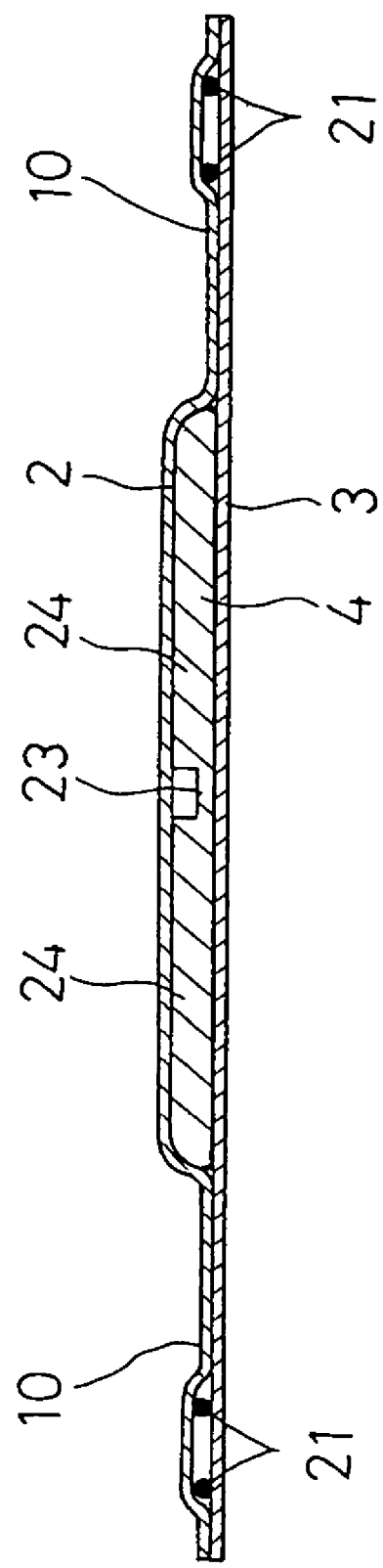
FIG. 7 is a sectional view taken along a line VII—VII in FIG. 6.

FIG. 5 is a perspective view showing a wearing article 1B according to an alternative embodiment of the invention with its front waist region 5 partially cut away, FIG. 6 is a partially cutaway developed plan view showing the article 1B with its transversely opposite lateral zones 10 disconnected and FIG. 7 is a sectional view taken along a line VII—VII in FIG. 6. In FIGS. 5 and 6, a transverse direction is indicated by an arrow L, a longitudinal direction is indicated by an arrow M and a leg-surrounding direction is indicated by an arrow N (only in FIG. 5). The article 1B comprises a liquid-pervious topsheet 2, a liquid-impervious backsheet 3 and a liquid-absorbent core 4 interposed between these sheets 2, 3 and attached to the inner surface of at least one of these sheets 2, 3 so as to define a front region 5, a rear waist region 7 and a crotch region 6 extending between these waist regions 5, 7. As will be seen in FIG. 6, the article 1B is formed with a pair of first longitudinal fold guiding lines 15 and a pair of second longitudinal fold guiding lines 16.

The article 1B is folded along the first fold guiding lines 15 and the second fold guiding lines 16, and a first zone 17 defined between a pair of the first fold guiding lines 15 and a second zone 17 defined between a pair of the second fold guiding lines 16 are tucked inwardly of the article 1B along the first and second fold guiding lines 15, 16.

The article 1B is distinguished from the article 1A shown in FIG. 1 in that the core 4 is formed with a longitudinal fold guiding zone 23. The fold guiding zone 23 extends in the longitudinal direction in coincidence with the imaginary fold guiding line 19 bisecting respective widths of the first and second zones 17, 18. In the fold guiding zone 23, the core 4 has a basis weight lower than that in a remaining zone 24 of the core 4 except for the fold guiding zone 23 and has stiffness lower than that in the remaining zone 24 of the core 4.

In the case of the article 1B, the core 4 is folded along the fold guiding zone 23 as the first and second zones 17, 18 are tucked inwardly of the article 1B. In this way, the fold guiding zone 23 facilitates the first and second zones 17, 18 to be tucked, on one hand, and prevents the first and second zones 17, 18 from being readily unfolded, on the other hand.

Tucking of the first and second zones 17, 18 inwardly of the article 1B along the first and second fold guiding lines 15, 16 allows the article 1B to be made compact. In the article 1B in which the first and second zones 17, 18 are tucked inwardly of the article 1B along the first and second fold guiding lines 17, 18, as will be seen in FIG. 5, and the leg-holes 14 remain opened and it is not likely that any troublesome handling might be required to put the article 1B on the wearer's body because it is unnecessary to open out these leg-holes 14 when the wearer's legs are guided through these leg-holes 14.

Figure 8:
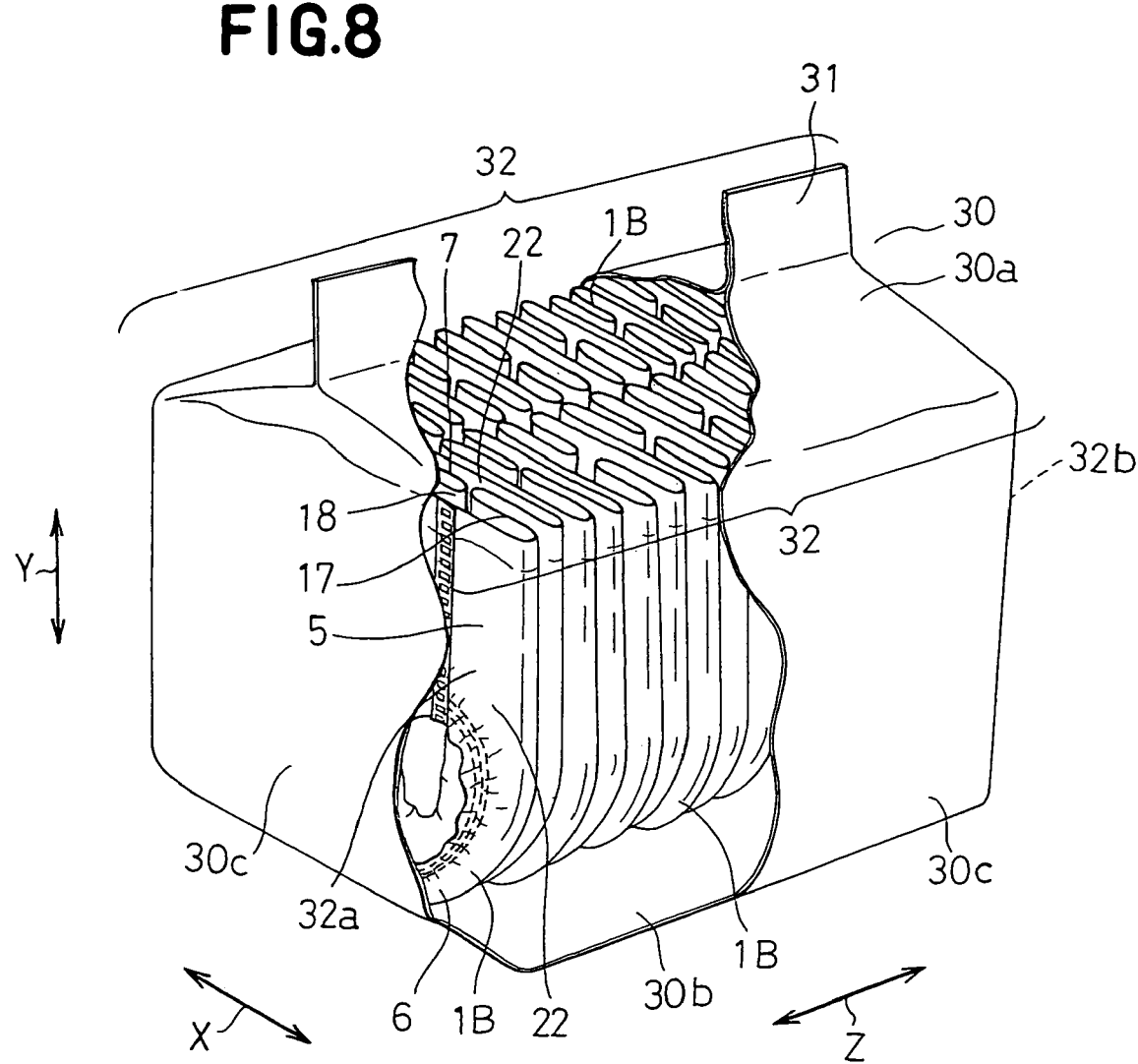
FIG. 8 is a partially cutaway perspective view showing the package packing therein a plurality of the articles each shown in FIG. 5.

FIG. 8 is a partially cutaway perspective view showing a package 30 packing therein a plurality of the articles 1B each shown in FIG. 5. In FIG. 8, a transverse direction is indicated by an arrow X, a longitudinal direction is indicated by an arrow Y and a back-and-forth direction is indicated by an arrow Z. Within the package 30, sixteen articles 1B are compactly packed.

Within the package 30, eight articles 1B are placed one against another in the back-and-forth direction so as to form a row 32 and a pair of rows 32 are packed side by side. In each of the rows 32, each pair of the articles 1B adjacent to each other in the back-and-forth direction (in one direction) are held in contact with each other over remaining zones 22 except for the first and second zones 17, 18 in the respective articles 1B.

Within the package 30, a force in a range of 10 to 75 N is exerted inward in the back-and-forth direction (inward in one direction) between the opposite ends 32a, 32b of the row 32 and a force required to pull one article 1B out from the row 32 of the articles 1B packed therein is 18 N or lower and a force required to pull the first article 1B out from the row 32 is in a range of 18 to 15 N. The force exerted inward in the back-and-forth direction (inward in one direction) between the opposite ends 32a, 32b of the row 32 as well as the force required to pull one of the articles 1B from the row 32 were measured by the method as has previously been described.

The package 30 contains therein a plurality of the articles 1B each having the first and second zones 17, 18 tucked so that an area over which each pair of the adjacent articles 1B held in contact with each other may be reduced and correspondingly a frictional force generated between these adjacent articles 1B may be alleviated compared to the case in which a plurality of articles 1B are packed in the package 30 without being tucked. It is possible to pull the article 1B with the force of 18 N or lower, particularly, to pull the first article 1B out from the row 32 easily regardless of the fact that a force in a range of 10 to 75 N is exerted inward in the back-and-forth direction between the opposite ends of the row 32.

While sixteen articles 1A or 1B are packed within the package 30, the number of the articles 1A or 1B to be packed within the package 30 is not limited to sixteen so far as a plurality of the articles 1A or 1B (eight or more articles 1A or 1B) form the row 32 in one direction.

While the force necessary to pull the article 1A or 1B out from the row 32 was measured by pulling the article 1A or 1B gripped by the chuck out from the row 32 toward above the package 30 using the tensile tester, it is also possible to measure the force by pulling the article 1A or 1B gripped by the chuck out from the row 32 laterally of the package 30 using the tensile tester. In this case also, the force required to pull one of the articles 1A or 1B out from the row 32 is 18 N or lower and the force required to pull the first article 1A or 1B out from the row 32 is in a range of 18 to 15 N.

A stock material for the topsheet 2 may be selected from the group consisting of a hydrophilic fibrous nonwoven fabric, a hydrophobic fibrous nonwoven fabric having a plurality of apertures and a plastic film having a plurality of fine perforations. A stock material for the backsheet 3 may be selected from the group consisting of a hydrophobic fibrous nonwoven fabric, a breathable but liquid-impervious plastic film, a composite nonwoven fabric comprising two or more hydrophobic fibrous nonwoven fabric layers laminated one upon another and a composite sheet comprising a hydrophobic fibrous nonwoven fabric and a breathable but liquid-impervious plastic film laminated upon each other. It is also possible to use, as a stock material for the backsheet 3, a composite nonwoven fabric comprising a melt blown fibrous nonwoven fabric having a high water-resistance interposed between two layers of spun bond fibrous nonwoven fabric being high in strength as well as in flexibility.

The nonwoven fabric may be selected from the group consisting of those obtained by spun lace-, needle punch-, melt blown-, thermal bond-, spun bond-, chemical bond- and air-through-processes. The component fibers of the nonwoven fabric may be selected from the group consisting of polyolefin-, polyester- and polyamide-based fibers, core-sheath type or side-by-side conjugated fibers of polyethylene/polypropylene or polyethylene/polyester.

The core 4 is a mixture of fluff pulp and super-absorbent polymer particles or a mixture of fluff pulp, super-absorbent polymer particles and thermoplastic synthetic resin fibers, in both cases, compressed to a desired thickness. Preferably, the core 4 is entirely wrapped with a liquid-pervious sheet such as a tissue paper or a hydrophilic fibrous nonwoven fabric to prevent the core 4 from getting out of its initial shape and to prevent polymer particles from falling off. The polymer particles may be selected from the group consisting of those of starch-based polymer, cellulose-based polymer and synthetic polymer. To reduce a basis weight of the core 4 in the fold guiding zone 23, a basis weight of fluff pulp and thermoplastic resin fibers constituting the core 4 in the fold guiding zone 23 may be made lower than that in the remaining zone 24 except for the fold guiding zone 23.

The steps of joining the top- and backsheets 2, 3 to each other, attaching the core 4 to these sheets 2, 3 and attaching the elastic members 20, 21 to these sheets 2, 3 may be carried out using a hot melt adhesive or various thermal welding techniques such as a heat-sealing and an ultrasonic sealing.

The pull-on disposable wearing article according to the present invention is primarily characterized in that the first and second zones are tucked inwardly of the article along the first and second fold guiding lines so that the article can be made compact. In addition, as the leg-holes remain opened, it is unnecessary to broaden the leg-holes in order to guide the wearer's legs through the leg-holes and any troublesome handling can be avoided when the article is put on the wearer's body.

In the case of the embodiment in which the core is formed with the fold guiding zone extending in the longitudinal direction, the core is folded along this fold guiding zone as the first and second zones are tucked inward of the article. In this way, the fold guiding zone facilitates the first and second zones to be tucked, on one hand, and prevents the first and second zones from being readily unfolded, on the other hand.

With the package packing therein a plurality of the articles each having the first and second zones tucked, an area over which each pair of the adjacent articles held in contact with each other may be reduced and correspondingly a frictional force generated between these adjacent articles may be alleviated compared to the case in which a plurality of the articles are packed in the package without being tucked. Consequently, a force of 18 N or lower is enough to pull the article, particularly, the first article out from the row of the articles regardless of the fact that a force in a range of 10 to 75 N is exerted inward in the back-and-forth direction from the opposite ends of the row.

What is claimed is:

1. A pull-on disposable wearing article, comprising:
   front and rear waist regions opposed to each other and a crotch region extending in a longitudinal direction of said article between said waist regions which are connected to each other along transversely opposite lateral zones thereof so as to form a waist-hole and a pair of leg-holes;
   a pair of first longitudinal fold guiding lines extending from a transversely middle zone of said crotch region into a transversely middle zone of said front waist region;
   a pair of second longitudinal fold guiding lines extending from said transversely middle zone of said crotch region into a transversely middle zone of said rear waist region;
   a first zone defined between said first fold guiding lines being tucked inwardly of said article, and a second zone defined between said second fold guiding lines being tucked inwardly of said article; and
   a third fold guiding line extending in said longitudinal direction and being located between said first fold guiding lines in the transversely middle zone of said front waist region and between said second fold guiding lines in the transversely middle zone of said rear waist region, wherein both said front and rear waist regions are folded along said third fold guiding line;
   wherein all said first, second and third fold guiding lines meet at one point that defines a pointed bottom of said folded article with said first and second zones being tucked inwardly.

2. A pull-on disposable wearing article, comprising:
   front and rear waist regions opposed to each other and a crotch region extending in a longitudinal direction of said article between said waist regions which are connected to each other along transversely opposite lateral zones thereof so as to form a waist-hole and a pair of leg-holes;
   a pair of first longitudinal fold guiding lines extending from a transversely middle zone of said crotch region into a transversely middle zone of said front waist region;
   a pair of second longitudinal fold guiding lines extending from said transversely middle zone of said crotch region into a transversely middle zone of said rear waist region;
   a first zone defined between said first fold guiding lines being tucked inwardly of said article, and a second zone defined between said second fold guiding lines being tucked inwardly of said article; and
   a third fold guiding line extending in said longitudinal direction and being located between said first fold guiding lines in the transversely middle zone of said front waist region and between said second fold guiding lines in the transversely middle zone of said rear waist region, wherein both said front and rear waist regions are folded along said third fold guiding line;
   wherein
   each of said first fold guiding lines has a waist section and a crotch section;
   the waist sections of said first fold guiding lines extend in parallel; and
   the crotch sections of said first fold guiding lines extend from the respective waist sections and converge towards the transversely middle zone of said crotch region.

3. The wearing article according to claim 2, wherein
   each of said second fold guiding lines has a waist section and a crotch section;
   the waist sections of said second fold guiding lines extend in parallel; and
   the crotch sections of said second fold guiding lines extend from the respective waist sections and converge towards the transversely middle zone of said crotch region.

4. A pull-on disposable wearing article, comprising:
   front and rear waist regions opposed to each other and a crotch region extending in a longitudinal direction of said article between said waist regions which are connected to each other along transversely opposite lateral zones thereof so as to form a waist hole and a pair of leg holes;
   a pair of first longitudinal fold guiding lines extending from a transversely middle zone of said crotch region into said front waist region;
   a pair of second longitudinal fold guiding lines extending from said transversely middle zone of said crotch region into said rear waist region;
   said front waist region being folded along said first fold guiding lines and a transversely middle zone of said front waist region located between said first fold guiding lines being tucked inwardly of said article; and
   said rear waist region being folded along said second fold guiding lines and a transversely middle zone of said rear waist region located between said second fold guiding lines being tucked inwardly of said article;
   wherein
   said first and second fold guiding lines define an outer contour of said folded article; and
   all said first and second fold guiding lines meet at one point that defines a pointed bottom of said folded article with the transversely middle zones of said front and rear waist regions being tucked inwardly.

5. A pull-on disposable wearing article, comprising:
   front and rear waist regions opposed to each other and a crotch region extending in a longitudinal direction of said article between said waist regions which are connected to each other along transversely opposite lateral zones thereof so as to form a waist hole and a pair of leg holes;

a pair of first longitudinal fold guiding lines extending from a transversely middle zone of said crotch region into said front waist region;

a pair of second longitudinal fold guiding lines extending from said transversely middle zone of said crotch region into said rear waist region;

said front waist region being folded along said first fold guiding lines and a transversely middle zone of said front waist region located between said first fold guiding lines being tucked inwardly of said article; and said rear waist region being folded along said second fold guiding lines and a transversely middle zone of said rear waist region located between said second fold guiding lines being tucked inwardly of said article;

wherein said first and second fold guiding lines define an outer contour of said folded article;

each of said first fold guiding lines has a waist section and a crotch section;

the waist sections of said first fold guiding lines extend in parallel; and the crotch sections of said first fold guiding lines extend from the respective waist sections and converge towards the transversely middle zone of said crotch region.

6. A pull-on disposable wearing article, comprising:

front and rear waist regions opposed to each other and a crotch region extending in a longitudinal direction of said article between said waist regions which are connected to each other along transversely opposite lateral zones thereof so as to form a waist hole and a pair of leg holes;

a pair of first longitudinal fold guiding lines extending from a transversely middle zone of said crotch region into said front waist region;

a pair of second longitudinal fold guiding lines extending from said transversely middle zone of said crotch region into said rear waist region;

said front waist region being folded along said first fold guiding lines and a transversely middle zone of said front waist region located between said first fold guiding lines being tucked inwardly of said article; and said rear waist region being folded along said second fold guiding lines and a transversely middle zone of said rear waist region located between said second fold guiding lines being tucked inwardly of said article;

wherein said first and second fold guiding lines define an outer contour of said folded article;

the wearing article further comprises a third fold guiding line extending in said longitudinal direction and being located between said first fold guiding lines in the transversely middle zone of said front waist region and between said second fold guiding lines in the transversely middle zone of said rear waist region, wherein the transversely middle zones of both said front and rear waist regions are further folded along said third fold guiding line;

each of said second fold guiding lines has a waist section and a crotch section;

the waist sections of said second fold guiding lines and the third fold guiding line extend in parallel; and the crotch sections of said second fold guiding lines and the third fold guiding line converge towards the transversely middle zone of said crotch region.

* * * * *